US007648639B2

(12) United States Patent
Holmes et al.

(10) Patent No.: US 7,648,639 B2
(45) Date of Patent: Jan. 19, 2010

(54) METHOD FOR SEPARATING A VOLUME OF COMPOSITE LIQUID INTO AT LEAST TWO COMPONENTS

(75) Inventors: Brian M. Holmes, Evergreen, CO (US); Peter Pihlstedt, Stockholm (SE); Geert Van Waeg, Brussels (BE)

(73) Assignee: CaridianBCT, Inc, Lakewood, CO (US)

( * ) Notice: Subject to any disclaimer, the term of this patent is extended or adjusted under 35 U.S.C. 154(b) by 230 days.

(21) Appl. No.: 11/956,696

(22) Filed: Dec. 14, 2007

(65) Prior Publication Data

US 2008/0093312 A1    Apr. 24, 2008

Related U.S. Application Data

(60) Division of application No. 10/783,831, filed on Feb. 20, 2004, now Pat. No. 7,347,932, which is a continuation-in-part of application No. 10/648,559, filed on Aug. 25, 2003, now Pat. No. 7,166,217.

(51) Int. Cl.
B04B 1/00 (2006.01)
B04B 3/00 (2006.01)
(52) U.S. Cl. .................. 210/739; 210/782; 210/104; 494/37; 494/45; 604/6.15
(58) Field of Classification Search .............. 210/739, 210/782, 104; 494/37, 45; 604/6.15
See application file for complete search history.

(56) References Cited

U.S. PATENT DOCUMENTS 3,297,244 A    1/1967  Hein
3,326,458 A    6/1967  Merman et al.
3,679,128 A    7/1972  Unger et al.

(Continued)

FOREIGN PATENT DOCUMENTS

DE        19728089        1/1999

(Continued)

OTHER PUBLICATIONS

"Preliminary Report on Patentability", PCT/US05/04252, Jul. 12, 2005.

(Continued)

*Primary Examiner*—David A Reifsnyder
(74) *Attorney, Agent, or Firm*—Edna M O'Connor; John R. Merkling; Laura B. Arciniegas

(57) ABSTRACT

A method for separating a volume of a composite liquid into at least a first component and a second component is performed in a centrifuge cooperating with a separation bag containing the volume of composite liquid. The separation bag is connected to at least a first component bag and a second component bag. The separation bag is spun so as to centrifuge the volume of composite liquid and cause the sedimentation of the at least first and second components. When the at least first and second components have sedimented, the first component is transferred at least one first transfer flow rate into the first component bag. When the first component has been transferred into the first component bag, the second component is transferred into the intermediate component bag at least one second transfer flow rate that is different from the at least one first transfer flow rate.

24 Claims, 5 Drawing Sheets

U.S. PATENT DOCUMENTS

| | | |
|---|---|---|
| 3,708,110 A | 1/1973 | Unger et al. |
| 3,724,747 A | 4/1973 | Unger et al. |
| 3,737,096 A | 6/1973 | Jones et al. |
| 3,858,796 A | 1/1975 | Unger et al. |
| 3,987,961 A | 10/1976 | Sinn et al. |
| 4,389,207 A | 6/1983 | Bacehowski et al. |
| 4,405,079 A | 9/1983 | Schoendorfer |
| 4,421,503 A | 12/1983 | Latham, Jr. et al. |
| 4,482,342 A | 11/1984 | Lueptow et al. |
| 4,720,284 A | 1/1988 | McCarty |
| 4,850,995 A | 7/1989 | Tie et al. |
| 4,990,132 A | 2/1991 | Unger et al. |
| 5,114,396 A | 5/1992 | Unger et al. |
| 5,427,695 A | 6/1995 | Brown |
| 5,632,906 A | 5/1997 | Ishida et al. |
| 5,723,050 A | 3/1998 | Unger et al. |
| 5,874,208 A | 2/1999 | Unger |
| 5,964,724 A | 10/1999 | Rivera et al. |
| 6,261,217 B1 | 7/2001 | Unger et al. |
| 6,296,602 B1 | 10/2001 | Headley |
| 6,315,706 B1 | 11/2001 | Unger et al. |
| 6,348,031 B1 | 2/2002 | Unger et al. |
| 6,500,107 B2 | 12/2002 | Brown et al. |
| 6,605,223 B2 | 8/2003 | Jorgensen et al. |
| 6,656,105 B2 | 12/2003 | Hogberg et al. |
| 7,166,217 B2 * | 1/2007 | Holmes et al. ............... 210/782 |
| 7,347,932 B2 * | 3/2008 | Holmes et al. ............... 210/782 |
| 2002/0119880 A1 | 8/2002 | Hogberg et al. |
| 2004/0026341 A1 * | 2/2004 | Hogberg et al. ............. 210/782 |

FOREIGN PATENT DOCUMENTS

| | | |
|---|---|---|
| EP | 0499891 | 8/1992 |
| EP | 0771569 | 5/1997 |
| WO | WO92/00145 | 1/1992 |
| WO | WO00/54823 | 9/2000 |
| WO | WO01/02037 | 1/2001 |
| WO | WO01/97943 | 12/2001 |
| WO | WO03/089027 | 10/2003 |
| WO | WO03/106040 | 12/2003 |
| WO | WO2004/018021 | 3/2004 |

OTHER PUBLICATIONS

"International Search Report", PCT/us05/04252, Jul. 12, 2005.
"European Search Report", EP05003022.0, Jan. 30, 2006.

* cited by examiner

METHOD FOR SEPARATING A VOLUME OF COMPOSITE LIQUID INTO AT LEAST TWO COMPONENTS

CROSS REFERENCE TO PRIOR APPLICATIONS

The present patent application is a divisional of U.S. patent application Ser. No. 10/783,831, filed Feb. 20, 2004, now U.S. Pat. No. 7,347,932 which is a continuation in part of U.S. patent application Ser. No. 10/648,559 filed on Aug. 25, 2003, now U.S. Pat. No. 7,166,217.

BACKGROUND OF THE INVENTION

1. Field of the Invention

The present invention relates to an apparatus and a method for separating a volume of composite liquid into at least two components.

The apparatus and a method of the invention are particularly appropriate for the separation of biological fluids comprising an aqueous component and one or more cellular components. For example, potential uses of the invention include: extracting a platelet component and a red blood cell component from a volume of filtered blood obtained by flowing of a volume of whole blood through a filter removing platelets and white blood cells therefrom; extracting a plasma component, a platelet component and a red blood cell component from a volume of filtered blood obtained by flowing a volume of whole blood through a filter removing white blood cells therefrom; extracting a plasma component an acellular component (including platelets white blood cells, and red blood cells) from a volume of whole blood, the cellular component being subsequently filtered so as to remove platelets and white blood cells therefrom; extracting a plasma component, a platelet component and a red blood cell component from a volume of whole blood, the white blood cells being subsequently removed by filtration from the platelet component and the red blood cell component.

2. Description of the Related Art

An apparatus for processing blood components is known from document WO 03/089027. This apparatus comprises a centrifuge adapted to cooperate with an annular separation bag connected to at least one product bag, e.g. a platelet component bag. The centrifuge includes: a rotor having a turntable for supporting the separation bag, and a central compartment for containing the product bag connected to the separation bag; and a squeezing system for squeezing the separation bag and causing the transfer of a separated component (e.g. platelets suspended in a diluting solution) from the separation bag into the product bag.

An object of the present invention is to design a centrifugation apparatus that can perform an optimized separation process for separating, in a minimum amount of time, a composite fluid, such as whole blood, into at least two high quality components.

SUMMARY OF THE INVENTION

According to the invention, an apparatus for separating a volume of composite liquid into at least a first component and a second component comprises: a centrifuge having: a rotor comprising: a turntable for supporting a flexible separation bag containing the volume of composite liquid; and a central compartment for containing at least a first component bag and an second component bag connected to the separation bag; a squeezing member for squeezing the separation bag and causing the transfer of the first component from the separation bag into the first component bag and the transfer of the second component from the separation bag into the second component bag; a memory for storing at least one centrifugation speed allowing for the sedimentation of the at least first and second components in the separation bag, and information related to at least one first transfer flow rate of the first component into the first component bag and at least one second transfer flow rate of the second component into the second component bag, whereby the at least one first transfer flow rate and the at least one second transfer flow rate are different; and a control unit programmed; for receiving from the memory the at least one centrifugation speed and the information related to the at least one first transfer flow rate and the at least one second transfer flow rate; and for causing the rotor to rotate at the at least one centrifugation speed; and for causing, after sedimentation of the at least first and second components in the separation bag, the squeezing member to squeeze the separation bag so as to transfer the first component from the separation bag into the first component bag at the at least one first transfer flow rate, and to transfer the second component from the separation bag into the second component bag at the at least one second transfer flow rate.

More specifically, an apparatus for separating a volume of composite liquid into a first component, an intermediate component including a second component, and a third component comprises: a centrifuge having: a rotor comprising: a turntable for supporting a separation bag containing the volume of composite liquid; and a central compartment for containing at least a first component bag and an intermediate component bag connected to the separation bag; a squeezing member for squeezing the separation bag and causing the transfer of at least one portion of the first component from the separation bag into the first component bag and the transfer of the intermediate component from the separation bag into the intermediate component bag; a memory for storing at least one centrifugation speed allowing for the sedimentation of the first, the second and the third components in the separation bag, and information related to at least one first transfer flow rate of the first component into the first component bag and at least one second transfer flow rate of the intermediate component into the intermediate component bag, whereby the at least one first transfer flow rate and the at least one second transfer flow rate are different; and a control unit programmed: for receiving from the memory the at least one centrifugation speed and the information related to the at least one first transfer flow rate and the at least one second transfer flow rate; and for causing the rotor to rotate at the at least one centrifugation speed; and for causing, after sedimentation of the first, the second and the third components in the separation bag, the squeezing member to squeeze the separation bag so as to transfer the at least one portion of the first component from the separation bag into the first component bag at the at least one first transfer flow rate, and to transfer the intermediate component from the separation bag into the intermediate component bag at the at least one second transfer flow rate.

Other features of the apparatus according to the invention are as follows:

The squeezing member is further for causing the transfer of the third component into a third component bag connected to the separation bag; the memory is further for storing information related to at least one third transfer flow rate of the third component into the third component bag, whereby the at least one third transfer flow rate is different from the at least one second transfer flow rate; and the control unit is further programmed: for receiving from the memory the information related to the at least one third transfer flow rate; and for causing the squeezing member to squeeze the separation bag so as to transfer the third component from the separation bag into the third component bag at the at least one third transfer flow rate.

The at least one first transfer flow rate is a substantially constant flow rate.

The at least one second transfer flow rate comprises an initial flow rate and a final flow rate, the final flow rate being lower than the initial flow rate.

The at least one third transfer flow rate comprises an initial flow rate and a final flow rate, the final flow rate being lower than the initial flow rate.

In a first variant of the invention, the control unit is further programmed: for causing, upon sedimentation of the first, second, and third components in the separation bag, the squeezing member to squeeze the separation bag so as to transfer a first portion of the first component from the separation bag into the first component bag at the at least one first transfer flow rate, while a second portion of the first component remains in the separation bag; and for causing, after the transfer of the first portion of the first component into the first component bag, a variation of the centrifugation speed so as to mix the second component with the second portion of the first component and form the intermediate component.

In the first variant of the invention, the control unit is further programmed for causing the rotor to rotate at a first centrifugation speed during the transfer of the first portion of the first component from the separation bag into the first component bag; and causing a rapid decrease of the centrifugation speed from the first centrifugation speed to a second centrifugation speed so as to mix the second component with the second portion of the first component and form the intermediate component.

Alternately, in a second variant of the invention, the control unit is further programmed: for causing, upon sedimentation of the first, second and third components in the separation bag, the squeezing member to squeeze the separation bag so as to transfer a first portion of the first component from the separation bag into the first component bag at the at least one first transfer flow rate while a second portion of the first component remains in the separation bag; for causing, after the transfer of the first portion of the first component into the first component bag, a rapid decrease in the centrifugation speed from a first centrifugation speed to a second centrifugation speed so as to cause a mixing of the second component with the second portion of the first component and the third component; and for causing, after the mixing of the second component with the second portion of the first component and the third component, an increase in the centrifugation speed from the second centrifugation speed to a third centrifugation speed so as to separate the third component from an intermediate component comprising the second component and the second portion of the first component.

The control unit is further programmed for causing a transfer of air from the separation bag into one of the component bags before the transfer of the first component from the separation bag into the first component bag.

The apparatus further comprises: a first valve member mounted on the rotor for interacting with a first tube connecting the separation bag to the first component bag and selectively allowing or blocking a flow of first component therethrough; a second valve member mounted on the rotor for interacting with a second tube connecting the separation bag to the intermediate component bag and selectively allowing or blocking a flow of intermediate component therethrough; and a third valve member mounted on the rotor for interacting with a third tube connecting the separation bag to the third component bag and selectively allowing or blocking a flow of fluid component therethrough, wherein the control unit is further programmed for controlling the first, the second and the third valve members.

The apparatus further comprises: a first sensor for detecting the third component on a pathway of the intermediate component to the intermediate component bag; a second sensor for detecting the third component on a pathway of the intermediate component to the intermediate component bag upstream of the first sensor; and a third sensor for detecting the third component on a pathway of the first component to the first component bag.

The control unit is further programmed for causing the transfer of the at least one portion of the first component from the separation bag into the first component bag by causing: the first valve member to open; the second and third valve members to close; and the squeezing member to squeeze the separation bag until the third sensor detects the third component on a pathway of the first component to the first component bag.

The control unit is further programmed for causing the transfer of the intermediate component from the separation bag into the intermediate component bag by causing: the second valve member to open; the first and third valve members to close; and the squeezing member to squeeze the separation bag until the first sensor detects the third component on a pathway of the intermediate component to the intermediate component bag.

The control unit is further programmed for causing the transfer of the intermediate component at the initial flow rate until the second sensor detects the third component and at the final flow rate until the first sensor detects the third component.

The control unit is further programmed for causing the transfer of the third component from the separation bag into the third component bag by causing: the third valve member to open; the first and the second valve members to close; and the squeezing member to squeeze the separation bag until it is substantially empty.

The first sensor is also adapted to detect a liquid on a pathway from the separation bag to the third component bag, and the control unit is further programmed for causing a transfer of air from the separation bag into the third component bags by causing: the first and second valve members to close; the third valve member to open; and the squeezing member to squeeze the separation bag until the first sensor detects the first component.

The apparatus further comprises a lid that can be secured on the turntable for enclosing the flexible separation bag and the squeezing member comprises: a flexible diaphragm secured to the turntable, a pumping station for pumping a hydraulic fluid into and out of an expandable chamber delimited between the turntable and the flexible diaphragm, whereby the flexible separation bag is being squeezed against the lid when the hydraulic fluid is pumped into the expandable chamber; and a pressure sensor for sensing the pressure of the hydraulic fluid and detecting when the separation bag is substantially empty.

The control unit is further programmed for causing the transfer of the third component at a first flow rate until the hydraulic pressure measured by the pressure sensor reaches a determined pressure threshold, and at a second flow rate after the hydraulic pressure measured by the pressure sensor has reached the determined pressure threshold, the second flow rate being lower than the first flow rate.

According to the invention, a method for separating a volume of a composite liquid into at least a first component and a second component comprises the steps of: spinning a separation bag containing the volume of composite liquid so as to centrifuge the volume of composite liquid and cause the sedimentation of the at least first and second components; when the at least first and second components have sedimented, transferring at least one first transfer flow rate the first component into a first component bag connected to the separation bag; when the first component has been transferred into the first component bag, transferring at least one second transfer flow rate the second component into a second component bag connected to the separation bag, whereby the at least one first and at least one second transfer flow rates are different.

More specifically, a method for separating a volume of a composite liquid into a first component, an intermediate component including a second component, and a third component comprises the steps of: spinning a separation bag containing the volume of composite liquid at least one centrifugation speed so as to centrifuge the volume of composite liquid and cause the sedimentation of the first, second and third components; when the three components have sedimented, transferring at least one first transfer flow rate at least one portion of the first component into a first component bag connected to the separation bag; when the at least one portion of the first component has been transferred into the first component bag, transferring at least one second transfer flow rate the intermediate component into an intermediate component bag connected to the separation bag, whereby the at least one first and at least one second transfer flow rates are different.

Other features of the method according to the invention are as follows:

The method further comprises the step of transferring the third component from the separation bag into a third component bag connected to the separation bag at least one third transfer flow rate, whereby the at least one third transfer flow rate is different from the at least one second transfer flow rate.

The at least one first the transfer flow rate is a substantially constant flow rate.

The at least one second transfer flow rate comprises an initial flow rate and a final flow rate, the final flow rate being lower than the initial flow rate.

The at least one third transfer flow rate comprises an initial flow rate and a final flow rate, the final flow rate being lower than the initial flow rate.

The step of transferring the intermediate component into the intermediate component bag comprises the steps of: transferring the intermediate component into the intermediate component bag at the initial flow rate until the third component is detected at a first location on a pathway of the intermediate component to the intermediate component bag; and transferring the intermediate component into the intermediate component bag at the final flow rate until the third component is detected at a second location on a pathway of the intermediate component to the intermediate component bag, the first location being upstream of the second location.

The step of transferring at least one portion of the first component comprises transferring a first portion of the first component from the separation bag into the first component bag, while a second portion of the first component remains in the separation bag.

The method further comprises the step of mixing the second component with the second portion of the first component so as to form the intermediate component, after the transfer of the first portion of the first component into the first component bag.

In a first variant of the invention, the step of mixing the second component with the second portion of the first component comprises rapidly decreasing the centrifugation speed from a first centrifugation speed to a second centrifugation speed.

In a second variant of the invention, the step of mixing of the second component with the second portion of the first component comprises: rapidly decreasing the centrifugation speed from a first rotation speed to a second centrifugation speed that is substantially lower than the first centrifugation speed so as mix the second portion of the first component with the second component and the third component; and increasing the centrifugation speed from the second rotation speed to a third centrifugation speed that is lower than the first centrifugation speed so as to separate the first component from a mix of the second component with the second portion of the first component forming the intermediate component.

The method further comprises the step of transferring air from the separation bag into one of the component bags before transferring the first component from the separation bag into the first component bag.

The step of transferring the first component from the separation bag into the first component bag comprises: allowing a flow of the first component through a first tube connecting the separation bag to the first component bag; blocking a flow of the intermediate component through a second tube connecting the separation bag to the intermediate component bag; blocking a flow of the third component through a third tube connecting the separation bag to the third component bag; and squeezing the separation bag until the third component is detected on a pathway of the first component to the first component bag.

The step of transferring the intermediate component from the separation bag into the intermediate component bag comprises: blocking a flow of the first component through a first tube connecting the separation bag to the first component bag; allowing a flow of the intermediate component through a second tube connecting the separation bag to the intermediate component bag; blocking a flow of the third component through a third tube connecting the separation bag to the third component bag; and squeezing the separation bag until the third component is detected on a pathway of the intermediate component to the intermediate component bag.

The step of transferring the third component from the separation bag into the third component bag comprises: blocking a flow of the first component through a first tube connecting the separation bag to the first component bag; blocking a flow of the intermediate component through a second tube connecting the separation bag to the intermediate component bag; allowing a flow of the third component through a third tube connecting the separation bag to the third component bag; and squeezing the separation bag until it is substantially empty.

The step of squeezing the separation bag comprises: submitting the separation bag to a hydraulic pressure; and measuring the hydraulic pressure, wherein the step of transferring the third component from the separation bag into the third component bag comprises: transferring the third component at a first flow rate until the measured hydraulic pressure reaches a determined pressure threshold; and transferring the third component at a second flow rate after the measured hydraulic pressure has reached the determined pressure threshold, the second flow rate being lower than the first flow rate.

The method further comprises the step of transferring air from the separation bag into the third component bag before transferring the first component from the separation bag into the first component bag, said step comprising: blocking a flow of the first component through a first tube connecting the separation bag to the first component bag; blocking a flow of the intermediate component through a second tube connecting the separation bag to the intermediate component bag; allowing a flow of the third component through a third tube connecting the separation bag to the third component bag; and squeezing the separation bag until a liquid is detected on a pathway of the first component to the third component bag.

Other features and advantages of the invention will appear from the following description and accompanying drawings, which are to be considered exemplary only.

DETAILED DESCRIPTION

For the sake of clarity, the invention will be described with respect to a specific use, namely the separation of whole blood into a first component comprising plasma, a second component comprising platelets and a third component comprising red blood cell. It should be understood however that this specific use is exemplary only.

Figure 1:
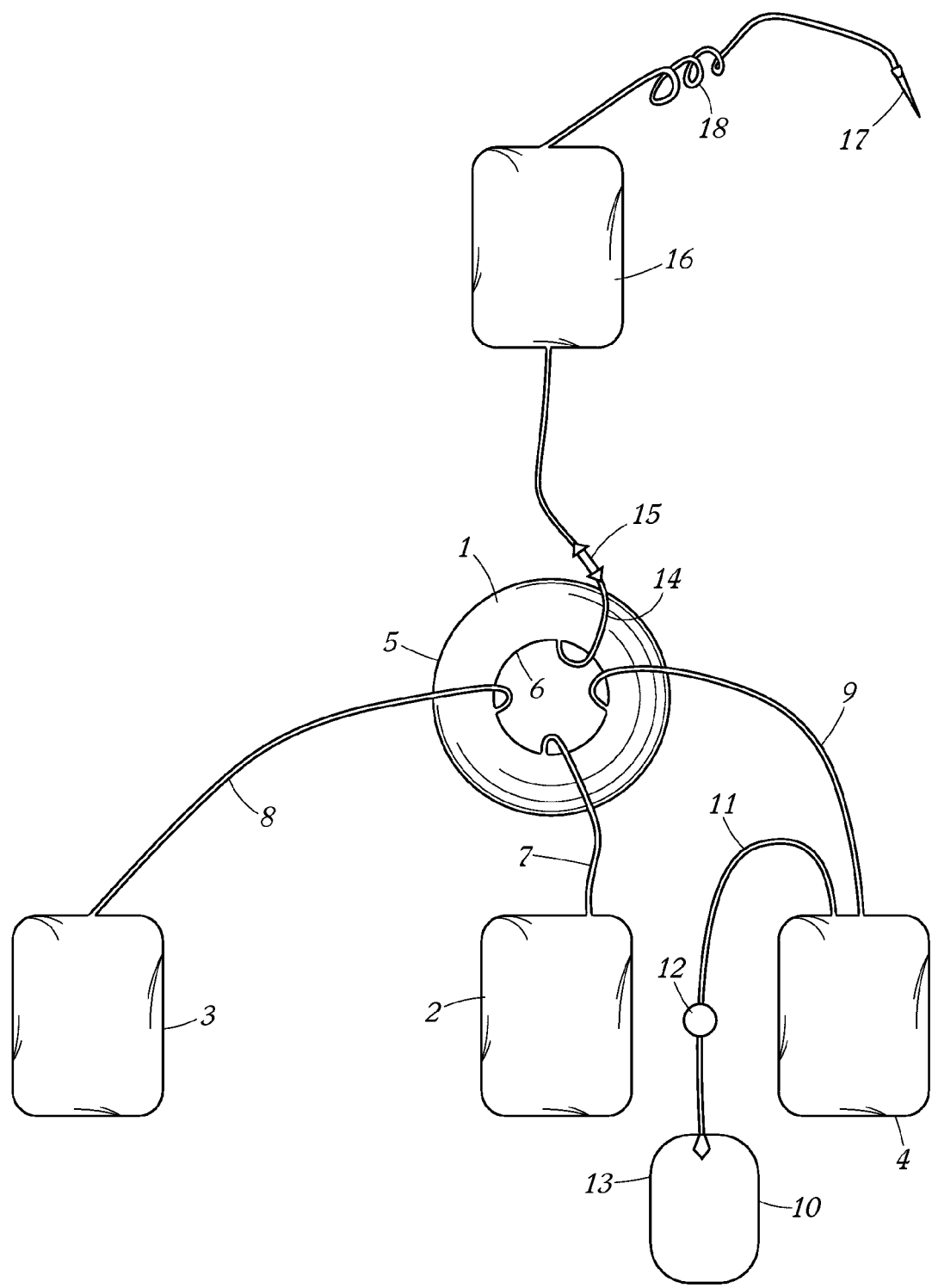
FIG. 1 is a schematic view of set of separation and collection bags designed for cooperating with a separation apparatus according to the invention.

A set of separation bags adapted to the separation of whole blood into a plasma product, a platelet product and red blood cell product is shown in FIG. 1. This set comprises a separation bag 1 and three product bags 2, 3, 4. The separation bag 1 is annular and has outer circular edge 5 and an inner circular edge 6. Variants of the separation bag include one or two radial walls extending from the inner edge 6 to the outer edge 5 so that the chamber defined within the bag, instead of being annular, has a C-shape with the C being more or less open. Also the separation bag can be shaped so as to fit either on a flat support surface or on a frusto-conical support surface of the rotor of a centrifuge. The first product bag 2, intended for containing the plasma product, is connected by a first tube 7 to the separation bag 1, at the inner edge 6 thereof. The second product bag 3, intended for containing the platelet product, is connected by a second tube 8 to the separation bag 1, at the inner edge 6 thereof. The third product bag 4, intended for containing the red blood cell product, is connected by a third tube 9 to the separation bag 1, at the inner edge 6 thereof. It is connected to a secondary bag 10 by a tube 11 having two segments respectively connected to the inlet and the outlet of a leukoreduction filter 12 (a filter for removing white blood cells). The secondary bag 10 contains a volume of storage solution for red blood cells. A plug 13 removable from within the secondary bag 10 (so-called "frangible pin", for example) blocks a liquid flow through the connecting tube 11 and prevents the storage solution from flowing into the third product bag 4. The bag set further comprises a supply tube 14 that is connected at one end to the separation bag 1, at the inner edge thereof. The other end of the supply tube 14 is either connected to a cannula, in which case the volume of blood to be separated is to be directly drawn from a donor into the separation bag 1, or connected directly or through a sterile connector 15 to a collection bag 16 connected in turn to a cannula 17 by a donor tube 18 (as shown in FIG. 1). The bag into which a volume of blood from a donor is to be directly transferred (the separation bag 1 or the collection bag 16) contains a volume of anti-coagulant solution (typically about 70 ml of a solution of sodium citrate for a blood donation of about 450 ml).

Figure 2:
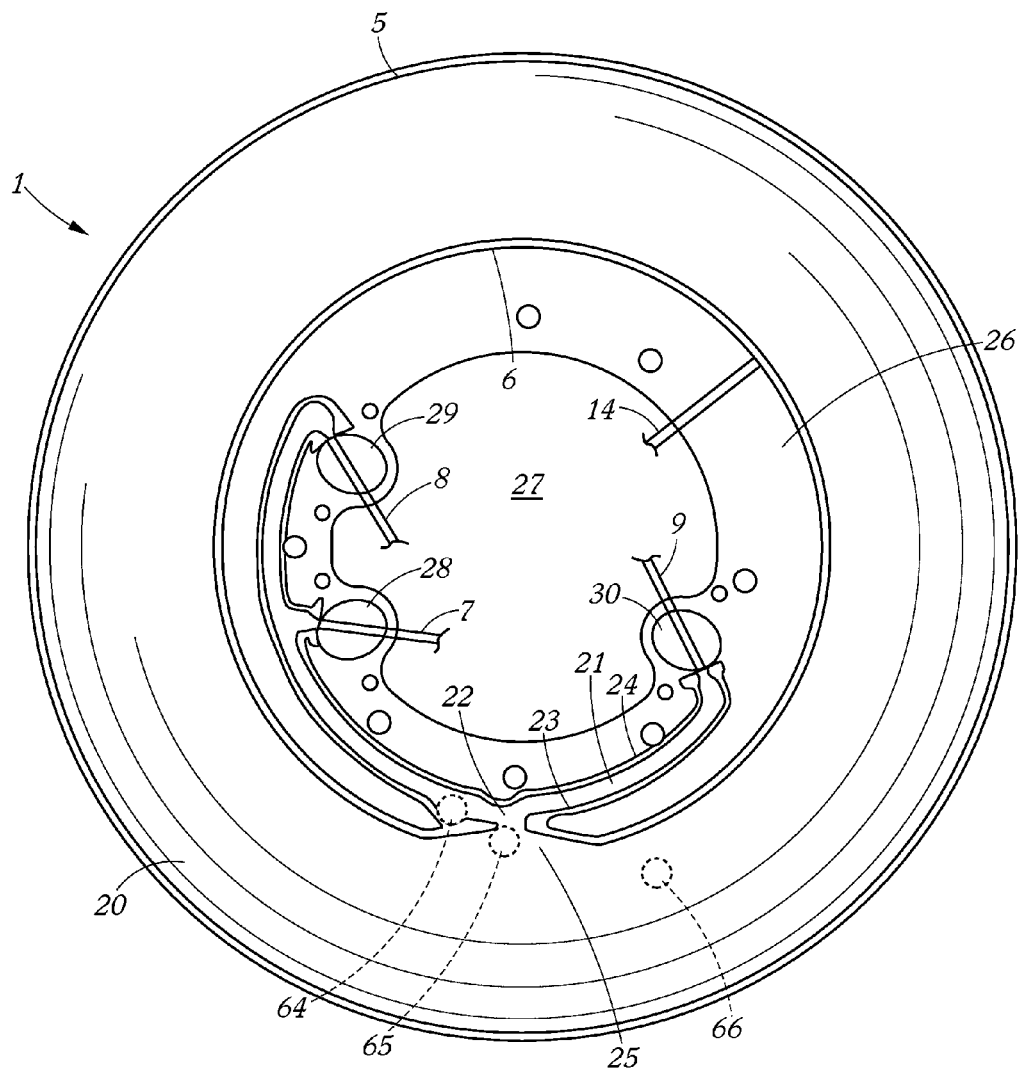
FIG. 2 is a top plan view of a separation bag designed for cooperating with a separation apparatus according to the invention.

FIG. 2 shows a separation bag 1, which is made of two superposed sheets of a flexible plastic material that are joined together by welded lines defining an annular chamber 20 communicating with an inner semi-circular distribution channel 21 via a narrow passage 22. More specifically, the annular chamber 20 is defined by a first circular welded line forming an outer edge 5, and a second circular welded line forming an inner edge 6, the two circular lines being substantially concentric. The distribution channel 21 is defined by two substantially parallel and semi-circular welded lines, forming an outer edge 23 and an inner edge 24 of the distribution channel 21. The inner edge 6 of the annular chamber and the outer edge 24 of the distribution channel 21 join in two points and define therebetween the passage 22. The inner edge 6 of the annular chamber 20 inwardly converges towards both junction points, and the resulting concavity in the otherwise circular inner edge 6 of the annular channel 20 defines a triangular bay area 25 in the annular chamber 20 just upstream of the passage 22.

The passage 22 opens in the distribution channel 21 at about two third of the length of the channel. With respect to the passage 22, the distribution channel 21 can therefore be defined as comprising a longer segment and a smaller segment that are interconnected and extend in opposite directions from the passage 22. The tube 9 connecting the product bag 4 for a red blood cell product to the separation chamber 1 is connected to the smaller segment of the channel 21, at the end thereof. The tube 8 connecting the product bag 3 for a platelet product to the separation chamber 1 is connected to the longer segment of the channel 21, at the end thereof. The tube 7 connecting the product bag 2 for a plasma product to the separation chamber 1 is connected to the longer segment of the channel 21, at about half of its length. The tube 14 for connecting a source of whole blood (donor or collection bag 16) to the separation bag 1 is connected to the annular chamber 1 at the inner edge 6 thereof, at about one third of the circumference of the inner edge 6 from the passage 22, in the same direction as the direction in which the small segment of the distribution channel 21 extends.

The distribution channel 21 and an end portion of the tubes 7, 8, 9, 14 are embedded in a disk-shaped support 26 made of a sheet of semi rigid plastic material, which is secured at its periphery to the inner edge 6 of the annular chamber 20. The disk-shaped support 26 comprises a large cut-out in the middle thereof, as well as three small circular cut-outs 28, 29, 30 adjacent to the connecting points of the tubes 7, 8, 9 to the distribution channel 21. The circular cut-outs 28, 29, 30 are positioned with respect to the end portion of tubes 7, 8, 9 so that each tube extends along a diameter of the corresponding circular cut-out and is therefore maintained straight over a portion of its length by the disk-shaped support 26.

Figure 3:
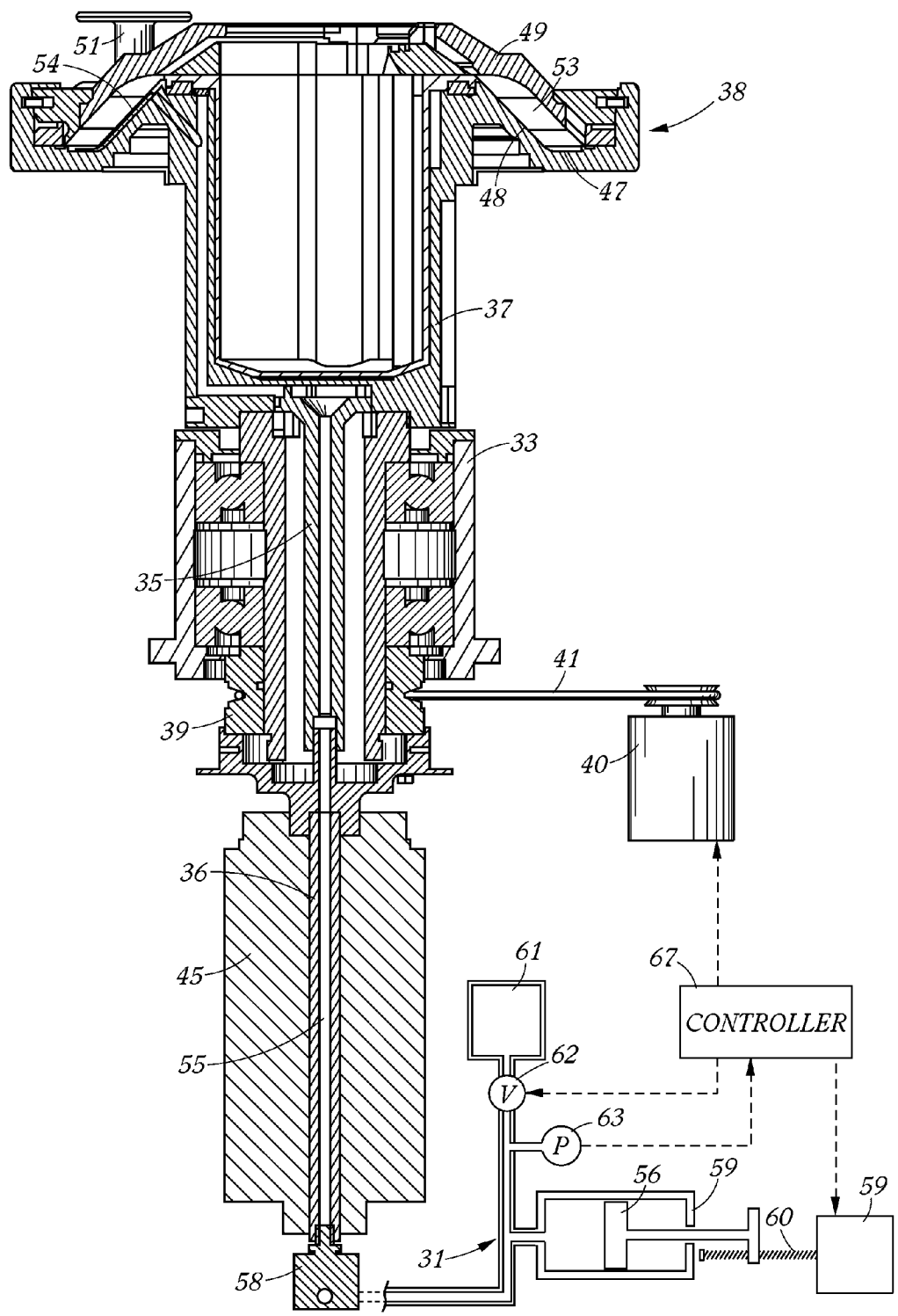
FIG. 3 is a schematic view, partly in cross-section, of a separation apparatus according to the invention.
Figure 4:
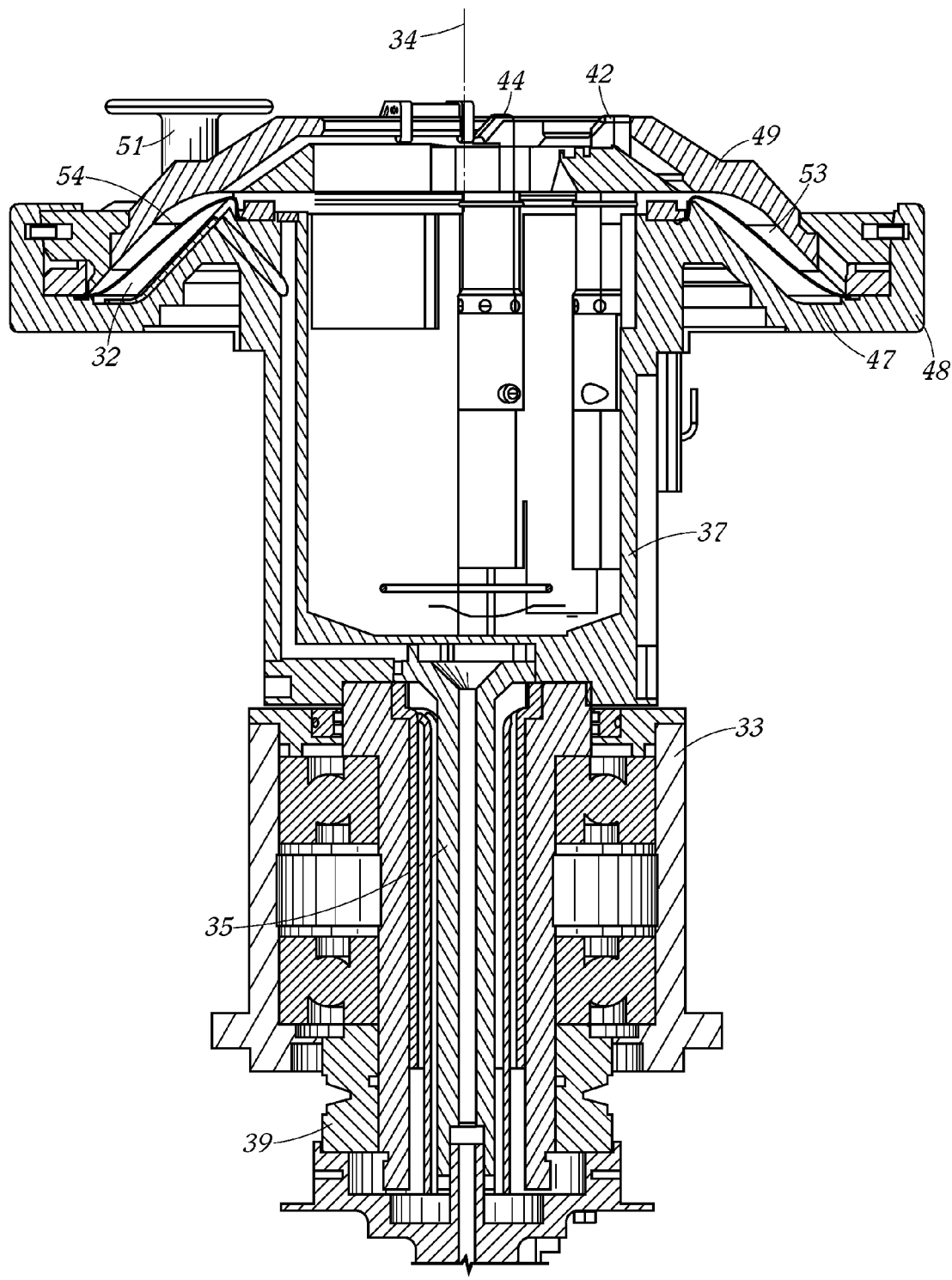
FIG. 4 is a cross-section view of the rotor of a separation apparatus according to the invention.
Figure 5:
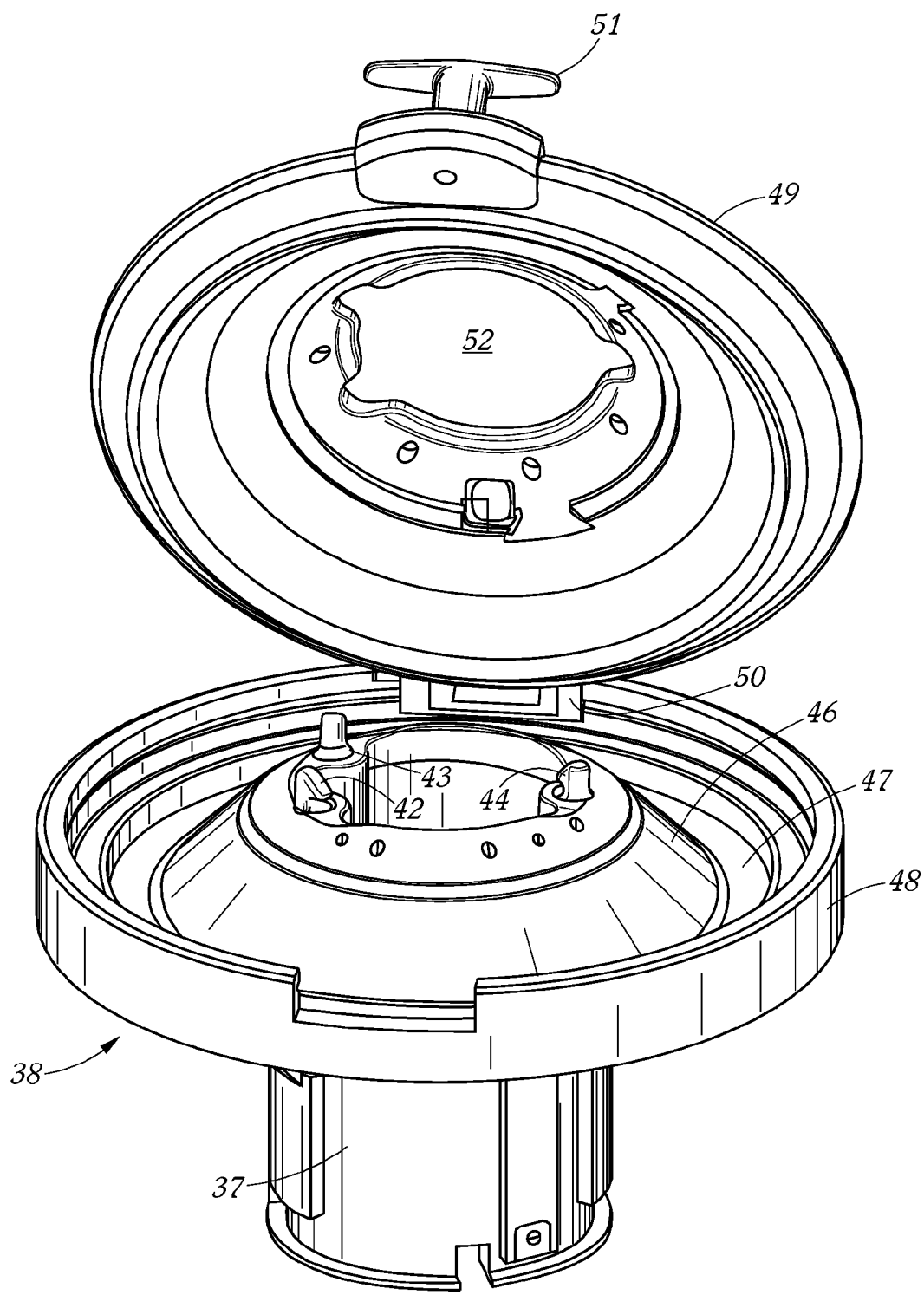
FIG. 5 is a perspective view of the upper part of the rotor of the separation apparatus of FIG. 4.

FIGS. 3, 4, 5 show an apparatus for separating a volume of composite liquid by centrifugation. The apparatus comprises a centrifuge adapted for receiving the set of separation and product bags shown in FIGS. 1 and 2, and a squeezing system for squeezing the separation bag and causing the transfer of separated components into the product bags.

The centrifuge comprises a rotor that is supported by a bearing assembly 33 allowing the rotor to rotate about a vertical central axis 34. The rotor comprises a cylindrical rotor shaft 35, 36, a cylindrical container 37 that is connected to the rotor shaft 35, 36 at the upper end thereof so that the longitudinal axis of the rotor shaft 35, 36 and the longitudinal axis of the container 37 are aligned with the central axis 34 of the rotor, and a circular turntable 38 connected to the container 37 at the upper end thereof so that the central axis of the turntable 37 is aligned with the central axis 34 of the rotor. The rotor shaft comprises a first upper portion 35 and a second lower portion 36. The upper portion 35 of the shaft extends in part through the bearing assembly 33. A pulley 39 is connected to the lower end of the upper portion 35 of the shaft.

The centrifuge further comprises a motor 40 coupled to the rotor by a belt 41 engaged in a groove of the pulley 39 so as to rotate the rotor about the central vertical axis 34.

The separation apparatus further comprises three pinch valve members 42, 43, 44 that are mounted on the rotor for selectively blocking or allowing a flow of liquid through a plastic tube, and selectively sealing and cutting a plastic tube. Each valve 42, 43, 44 comprises an elongated cylindrical body and a head having a groove that is defined by a stationary upper jaw and a lower jaw movable between an open and a closed position, the groove being dimensioned so that one of the plastic tubes 7, 8, 9 of the bag set shown in FIGS. 1 and 2 can be snuggly engaged therein when the lower jaw is in the open position. The elongated body contains a solenoid-actuated mechanism for moving the lower jaw and a radio frequency generator for providing the energy that is necessary for sealing and cutting a plastic tube. The pinch valve members 42, 43, 44 are mounted inside the cylindrical container 37, adjacent the interior surface thereof, so that their longitudinal axis is parallel to the central axis 34 of the rotor and their heads protrude above the rim of the container 37. The three circular cut-outs 28, 29, 30 of the support portion 26 of the separation bag 1 shown in FIG. 2 are so dimensioned and positioned as to allow for the engagement of the heads of the three pinch valve members 42, 43, 44 therethrough, with the portions of the tubes 7, 8, 9 extending across the circular cut-outs 28, 29, 30 oriented so as to face the groove in the heads of the pinch valve members 42, 43, 44. Electric power is supplied to the pinch valve members 42, 43, 44 through a slip ring 45 that is mounted around the lower portion 36 of the rotor shaft.

The turntable 38 comprises a central frusto-conical portion 46, the upper, smaller edge of which is connected to the rim of the container 37, an annular flat portion 47 connected to the lower, larger edge of the frusto-conical portion 46 and an outer cylindrical flange 48 extending upwards from the outer periphery of the annular portion 47. The turntable 38 further comprises a vaulted circular lid 49 that is secured to the flange 48 by a hinge 50 so as to pivot between an open and a closed position. The lid 49 is fitted with a lock 51 by which it can be blocked in the closed position. The lid 49 comprises a large cut-out 52 in its upper part that gives access to the cylindrical container 37 of the rotor. The lid 49 has an annular interior surface that is so shaped that, when the lid 49 is in the closed position, it defines with the frusto-conical portion 46 and the annular flat portion 47 of the turntable 38 a frusto-conical annular compartment 53 having a radial cross-section that has substantially the shape of a parallelogram. The frusto-conical annular compartment 53, later the "separation compartment", is intended for containing the separation chamber of the separation bag shown in FIG. 2.

The squeezing system for squeezing the separation bag within the separation compartment 53 and causing the transfer of separated components into the product bags comprises a flexible annular diaphragm 54 that is so shaped as to line the frusto-conical portion 46 and the annular flat portion 47 of the turntable 38, to which it is secured by gluing along its smaller and larger circular edges. The squeezing system further comprises a hydraulic pumping station 31 for pumping a hydraulic liquid in and out an expandable hydraulic chamber 32 defined between the flexible diaphragm 54 and the turntable 38, via a duct 55 extending through the rotor from the lower end of the lower portion 36 of the rotor shaft to the turntable 38. The pumping station 31 comprises a piston pump having a piston 56 movable in a hydraulic cylinder 57 fluidly connected via a rotary fluid coupling 58 to the rotor duct 55. The piston 56 is actuated by a stepper motor 59 that moves a lead screw 60 linked to the piston rod. The hydraulic cylinder 57 is also connected to a hydraulic liquid reservoir 61 having an access controlled by a valve 62 for selectively allowing the introduction or the withdrawal of hydraulic liquid into and from a hydraulic circuit including the hydraulic cylinder 57, the rotor duct 55 and the expandable hydraulic chamber 32. A pressure gauge 63 is connected to the hydraulic circuit for measuring the hydraulic pressure therein.

The separation apparatus further comprises three sensors 64, 65, 66 for detecting characteristics of the separation process occurring within a separation bag when the apparatus operates. The three sensors 64, 65, 66 are embedded in the lid 49 so as to face the separation bag 1 as shown in FIG. 2, when the lid 49 is closed. The first sensor 64 (later the "channel sensor") is embedded in the lid 49 so as to be positioned over the longer segment of the distribution channel 21. The channel sensor 64 is able to detect the presence of absence of liquid in the distribution channel 21 as well as to detect red blood cells in a liquid. The second sensor 65 (later the "bay sensor") is embedded in the lid 49 so as to be positioned over the bay area 25. The bay sensor 65 is able to detect red blood cells in a liquid. The third sensor 66 (later the "bag sensor") is embedded in the lid 49 so as to be positioned over the separation chamber 20, at about one third of the breadth of the separation chamber from the inner edge 6 of the separation chamber 20, slightly outside of the bay area 25 on the side of the smaller segment of the distribution channel 21. The bag sensor 66 is able to detect red blood cells in a liquid. Each sensor 64, 65, 66 can comprise a photocell including an infra-red LED and a photo-detector.

The separation apparatus further comprises a controller 67 including a microprocessor and a memory for providing the microprocessor with information and programmed instructions relative to the operation of the apparatus. In particular, the microprocessor is programmed for receiving information relative to the various centrifugation speeds at which the rotor is to be rotated during the various stage of a separation process, and information relative to the various transfer flow rates at which separated components are to be transferred from the separation bag 1 into the products bags 2, 3, 4. The information relative to the various transfer flow rates can be expressed, for example, as hydraulic liquid flow rates in the hydraulic circuit, or as rotation speeds of the stepper motor 59 of the hydraulic pumping station 31. The microprocessor is further programmed to receive, directly or through the memory, information from the pressure gauge 63 and from the photocells 64, 65, 66.

The microprocessor is further programmed for controlling the centrifuge motor 40, the stepper motor 59, and the pinch valve members 42, 43, 44 so as to cause the separation apparatus to operate as follows.

First stage: the volume of anti-coagulated blood to be separated is transferred into the separation bag before or after the disposable set is loaded in the centrifugation apparatus according to one of the following variants.

First variant: a volume of anti-coagulated blood to be separated (for example about 500 ml) is transferred into the separation bag before the disposable set is loaded in the centrifugation apparatus. After a clamp has been placed at the connection of each tubes 7, 8, 9 to the separation bag 1, a volume of anti-coagulated blood contained in a collection bag 16 is transferred by gravity in to the separation bag 1. The tube 14 connecting the collection bag 16 to the separation bag is sealed and cut. The separation bag 1 is fitted within the turntable 38, the tubes 8, 7, 9 are engaged in the pinch valve members 42, 44, 43, and the product bags 2, 3, 4, and the secondary bag 10 are placed into the container 37. The pinch valve members 42, 44, 43 are closed and the clamps on the tubes 7, 8, 9 are removed. Alternately, clamps are not placed on tubes 7, 8, 9 when pressure frangible seals are provided in both segments of the distribution channel 21 so as to prevent communication between the product bags 2, 3, 4 and the separation bag 1 as long as the pressure that builds within the separation bag during the operation of the separation apparatus is not high enough to break the frangible seals.

Second variant: same as the first variant, except that the separation bag 1, which contains a volume of anticoagulant, is directly connected to a donor and the blood of the donor is directly drawn into the separation bag 1, which is thus also used as a collection bag.

Second stage: the air present in the separation bag 1 is purged into the product bag 4 in which the red blood cell component is to be later transferred.

The pinch valve members 42, 44 are closed and the pinch valve member 43 in which the tube 9 is engaged is open. The rotor is set in motion by the centrifuge motor 40 and its rotation speed increases steadily until it rotates at a first, high centrifugation speed (for example, about 3200 RPM). Before the rotor rotates at the first centrifugation speed, the pumping station 31 is actuated so as to pump hydraulic liquid at a constant flow rate (for example, about 240 ml/min) into the hydraulic chamber 32 and consequently squeeze the separation bag 1. The air present in the separation bag 1 is expelled into the product bag 4 for the red blood cell component. When the channel sensor 64 detects a liquid in the distribution channel 21, the pumping station 31 is stopped and the pinch valve member 43 is closed.

When the distribution channel 21 of the separation bag 1 is initially closed by frangible seals, the transfer of air from the separation bag 1 into the product bag 4 occurs once the pressure building up in the separation bag 1 is high enough to cause the frangible seals to break.

Note that, alternately, the air contained in the separation bag 1 could be expelled into either the product bag 2 for the plasma component or the product bag 3 for the platelet component. It is however of interest to expel the air in the bag 4 for the red blood cell component because this will allow the red blood cell component to be later transferred by gravity from the product bag 4 into the secondary bag 10.

Third stage: the blood within the separation chamber is sedimented to a desired level.

At the onset of this stage, the three pinch valve members 42, 43 and 44 are closed. The rotor is rotated at the first high centrifugation speed (for example, about 3200 RPM) for a predetermined period of time (for example, about 220 seconds) that is selected so that, whatever the hematocrit of the volume of the blood initially transferred in the separation chamber 1, the blood sediments therein at the end of the selected period to a point where the hematocrit of the outer annular red blood cell layer is about 90 and the inner annular plasma layer plasma does not substantially contain anymore cells, the platelets and the white blood cells occupying then an intermediary annular layer between the red blood cell layer and the plasma layer.

Fourth stage: a first component (plasma component) is transferred into the product bag 2.

At the onset of this stage, the three pinch valve members 42, 43, 44 are closed. Throughout the fourth stage, the rotor is rotated at the first high centrifugation speed (for example, about 3200 RPM). After a predetermined period of time after the bag sensor 66 has stopped detecting red blood cells, which can happen before the end of the predetermined sedimentation period, the pinch valve member 44 controlling the access to the plasma component bag 4 is opened and the pumping station 31 is actuated so as to pump hydraulic liquid at a constant flow rate (for example, about 220 ml/min) into the hydraulic chamber 32 and consequently squeeze the separation bag 1 for a predetermined period of time so as to cause the transfer of a first portion of the plasma into the product bag 2, whereas a second portion of the plasma (for example, about 60 ml) remains in the separation bag 1.

The transfer flow rate of the plasma component (which is directly related to the flow rate of the hydraulic fluid) is selected to be as high as possible without disturbing the platelet layer so as to avoid contaminating the plasma component with platelets.

Fifth stage: an Intermediate component (platelet component) is prepared in the separation bag 1.

First variant: the pinch valve member 44 controlling the access to the plasma component bag 4 is open, and the pinch valve members 42, 43 are closed. The rotation speed of the rotor is rapidly decreased from the first centrifugation speed to a second centrifugation speed (for example, from about 3200 RPM to about 2000 RPM, within about 10 seconds) so as to form an intermediate component resulting from the suspension of the platelets into the second portion of the plasma, whereas the red blood cell layer and the suspended platelet layer remains substantially separated.

Second variant: the three pinch valve members 42, 43, 44 are closed. The rotation speed of the rotor is rapidly decreased from the first centrifugation speed to a second centrifugation speed (for example, from about 3200 RPM to about 1000 RPM, within about 20 seconds) so as to mix the red blood cells, the platelets and the second portion of the plasma. The rotation speed of the rotor is then increased from the second centrifugation speed to a third centrifugation speed, lower that the first centrifugation speed (for example, from about 1000 RPM to about 2500 RPM), so as to separate in the separation bag 1 a red blood cell component and an intermediate component comprising a suspension of platelets in plasma.

Sixth stage: the intermediate component (platelet component) is transferred into the product bag 3.

The pinch valve member 42 controlling the access to the platelet component bag 4 is open and the pinch valve members 43, 44 are closed. The rotor is rotated at the second centrifugation speed (for example, about 2000 RPM, if the preceding stage is the first variant of the fifth stage) or at the third rotation speed (for example, about 2500 RPM, if the preceding stage is the second variant of the fifth stage). The pumping station 31 is actuated so as to the pump hydraulic liquid at a first flow rate into the hydraulic chamber 32 and consequently squeeze the separation bag 1 so as to cause the transfer the platelet component into the product bag 3. The first flow rate (for example, about 140 ml/min) is substantially lower than the flow rate (for example, about 220 ml/min) at which the plasma component is transferred into the product bag 2 in the fourth stage. The first transfer flow rate of the platelet component (which is directly related to the first flow rate of the hydraulic fluid) is selected to be high enough for preventing the suspended platelets from sedimenting, without at the same time triggering the activation of the platelets.

When the bay sensor 65 detects red blood cells, the pumping station 31 is actuated so as to pump hydraulic liquid into the hydraulic chamber 32 at a second flow rate (for example 40 ml/min) that is substantially lower then the first flow rate, in order to prevent the contamination of the platelet component by red blood cells.

When the hydraulic liquid has been pumped into the hydraulic chamber 32 at the second flow rate for a predetermined period of time (for example, about 4 seconds), the pumping station is actuated so as to pump the hydraulic liquid at a third flow rate (for example, about 20 ml/min) that is lower than the second flow rate, until a predetermined period of time (for example, about 12 seconds) has lapsed after the channel sensor 64 has detected red blood cells. The pumping station 31 is then stopped.

Seventh stage: the third component (red blood cell component) is transferred into the product bag 4.

The pinch valve member 43 controlling the access to the red blood cell component bag 4 is open and the pinch valve members 42, 44 are closed. The rotation speed of the rotor is decreased from the second centrifugation speed (for example, about 2000 RPM) or the third centrifugation speed (for example, about 2500 RPM) to a fourth, lower, centrifugation speed (for example, about 1500 RPM). The pumping station 31 is actuated so as to pump hydraulic liquid at a first flow rate into the hydraulic chamber 32 and consequently squeeze the separation bag 1 so as to cause the transfer of the red blood cell component into the product bag 4. The first flow rate (for example, about 350 m/min) is substantially higher than the flow rate (for example, about 220 ml/min) at which the plasma component is transferred into the product bag 2 in the fourth stage. The first transfer flow rate of the red blood cell component (which is directly related to the flow rate of the hydraulic fluid) is selected to be as high as possible without damaging the red blood cells (hemolysis).

When the pressure of the hydraulic liquid measured by the pressure gauge 63 reaches a first high pressure threshold (for example, about 0.7 bar), the flow rate of the hydraulic liquid is decreased from the first flow rate to a second flow rate (for example, about 100 ml/min). When the pressure of the hydraulic liquid measured by the pressure gauge 63 reaches a second high pressure threshold (for example, about 1.6 bar), the flow rate of the hydraulic liquid is further decreased from the second flow rate to a third flow rate (for example, about 37 ml/min).

The second and third transfer flow rates of the red blood cell component (which are directly related to the flow rate of the hydraulic fluid) are selected so that a maximal portion of the red blood cell component is transferred into the red blood cell component bag 4.

When a predetermined period of time (for example, about 30 seconds) has lapsed after the pressure of the hydraulic liquid has reached the second pressure threshold, the rotation speed of the rotor is decreased until the rotor stops, the pumping station 31 is actuated so as to pump the hydraulic liquid from the hydraulic chamber 32 at a high flow rate (for example, about 800 ml/min) until it the hydraulic chamber 32 is empty, and the three pinch valve members 42, 43, 44 are actuated so as to seal and cut the tubes 7, 8, 9.

Any of the at least one first transfer flow rate for the plasma component (one flow rate in the example described above), the at least one second transfer flow rate for the platelet component (three successive flow rates in the example described above), the at least third first transfer flow rate for the red blood cell component (three successive flow rates in the example described above) may be substantially constant, as in the example described above, or it may vary and, for example, comprise a ramp or a series of small steps.

It will be apparent to those skilled in the art that various modifications can be made to the apparatus and method described herein. Thus, it should be understood that the invention is not limited to the subject matter discussed in the specification. Rather, the present invention is intended to cover modifications and variations.

The invention claimed is:

1. A method for separating a volume of a composite liquid into a first component, an intermediate component including a second component, and a third component, whereby the volume of composite liquid is contained in a separation bag connected to at least a first component bag and an intermediate component bag, the method comprising the steps of:
   spinning the separation bag at least one centrifugation speed so as to centrifuge the volume of composite liquid and cause the sedimentation of the first, second and third components;
   when the three components have sedimented, transferring at least one first transfer flow rate at least one portion of the first component into the first component bag;
   when the at least one portion of the first component has been transferred into the first component bag, transferring at least one second transfer flow rate the intermediate component into the intermediate component bag, whereby the at least one first and at least one second transfer flow rates are different.

2. A method according to claim 1, wherein the at least one first the transfer flow rate is a substantially constant flow rate.

3. A method according to claim 1, wherein the at least one second transfer flow rate comprises an initial flow rate and a final flow rate, the final flow rate being lower than the initial flow rate.

4. A method according to claim 3, wherein the step of transferring the intermediate component into the intermediate component bag comprises the steps of:
   transferring the intermediate component into the intermediate component bag at the initial flow rate until the third component is detected at a first location on a pathway of the intermediate component to the intermediate component bag; and
   transferring the intermediate component into the intermediate component bag at the final flow rate until the third component is detected at a second location on a pathway of the intermediate component to the intermediate component bag, the first location being upstream of the second location.

5. A method according to claim 1, wherein the step of transferring at least one portion of the first component comprises transferring a first portion of the first component from the separation bag into the first component bag, while a second portion of the first component remains in the separation bag.

6. A method according to claim 5, further comprising the step of mixing the second component with the second portion of the first component so as to form the intermediate component, after the transfer of the first portion of the first component into the first component bag.

7. A method according to claim 6, further comprising spinning the separation bag at a first centrifugation speed during the transfer of the first portion of the first component from the separation bag into the first component bag.

8. A method according to claim 7, wherein the step of mixing the second component with the second portion of the first component comprises rapidly decreasing the centrifugation speed from the first centrifugation speed to a second centrifugation speed.

9. A method according to claim 7, wherein the step of mixing of the second component with the second portion of the first component comprises:
rapidly decreasing the centrifugation speed from the first rotation speed to a second centrifugation speed that is substantially lower than the first centrifugation speed so as mix the second portion of the first component with the second component and the third component; and
increasing the centrifugation speed from the second rotation speed to a third centrifugation speed that is lower than the first centrifugation speed so as to separate the first component from a mix of the second component with the second portion of the first component forming the intermediate component.

10. A method according to claim 1, further comprising the step of transferring air from the separation bag into one of the component bags before transferring the first component from the separation bag into the first component bag.

11. A method according to claim 1, wherein the step of squeezing the separation bag comprises submitting the separation bag to a hydraulic pressure.

12. A method according to claim 1, wherein the composite liquid comprises whole blood, the first component comprises plasma, the second component comprises platelets, the third component comprise red blood cells and the intermediate component comprises a suspension of platelets in plasma.

13. A method according to claim 1, further comprising the step of transferring the third component from the separation bag into a third component bag connected to the separation bag at least one third transfer flow rate, whereby the at least one third transfer flow rate is different from the at least one second transfer flow rate.

14. A method according to claim 13, wherein the at least one third transfer flow rate comprises an initial flow rate and a final flow rate, the final flow rate being lower than the initial flow rate.

15. A method according to claim 13, further comprising spinning the separation bag during the transfer of the third component from the separation bag into the third component bag at a centrifugation speed that is less than a centrifugation speed during the transfer of the intermediate component into the intermediate component bag.

16. A method according to claim 13, wherein the step of transferring the first component from the separation bag into the first component bag comprises:
allowing a flow of the first component through a first tube connecting the separation bag to the first component bag;
blocking a flow of the intermediate component through a second tube connecting the separation bag to the intermediate component bag;
blocking a flow of the third component through a third tube connecting the separation bag to the third component bag; and
squeezing the separation bag until the third component is detected on a pathway of the first component to the first component bag.

17. A method according to claim 13, wherein the step of transferring the intermediate component from the separation bag into the intermediate component bag comprises:
blocking a flow of the first component through a first tube connecting the separation bag to the first component bag;
allowing a flow of the intermediate component through a second tube connecting the separation bag to the intermediate component bag;
blocking a flow of the third component through a third tube connecting the separation bag to the third component bag; and
squeezing the separation bag until the third component is detected on a pathway of the intermediate component to the intermediate component bag.

18. A method according to claim 13, wherein the step of transferring the third component from the separation bag into the third component bag comprises:
blocking a flow of the first component through a first tube connecting the separation bag to the first component bag;
blocking a flow of the intermediate component through a second tube connecting the separation bag to the intermediate component bag;
allowing a flow of the third component through a third tube connecting the separation bag to the third component bag; and
squeezing the separation bag until it is substantially empty.

19. A method according to claim 18, further comprising the steps of:
detecting when the separation bag is substantially empty, and
stopping spinning the separation bag after detecting that the separation bag is substantially empty.

20. A method according the claim 13, wherein the step of squeezing the separation bag comprises:
submitting the separation bag to a hydraulic pressure; and measuring the hydraulic pressure,
wherein the step of transferring the third component from the separation bag into the third component bag comprises:
transferring the third component at a first flow rate until the measured hydraulic pressure reaches a determined pressure threshold; and
transferring the third component at a second flow rate after the measured hydraulic pressure has reached the determined pressure threshold, the second flow rate being lower than the first flow rate.

21. A method according to claim 13, further comprising the step of transferring air from the separation bag into the third component bag before transferring the first component from the separation bag into the first component bag, said step comprising:
blocking a flow of the first component through a first tube connecting the separation bag to the first component bag;
blocking a flow of the intermediate component through a second tube connecting the separation bag to the intermediate component bag;
allowing a flow of the third component through a third tube connecting the separation bag to the third component bag; and
squeezing the separation bag until a liquid is detected on a pathway of the first component to the third component bag.

22. A method for separating a volume of a composite liquid into at least a first component and a second component, whereby the volume of composite liquid is contained in a separation bag connected to at least a first component bag and a second component bag, the method comprising the steps of:

spinning the separation bag so as to centrifuge the volume of composite liquid and cause the sedimentation of the at least first and second components;

when the at least first and second components have sedimented, transferring at least one first transfer flow rate the first component into the first component bag;

when the first component has been transferred into the first component bag, transferring at least one second transfer flow rate the second component into the second component bag, whereby the at least one first and at least one second transfer flow rates are different.

23. A method according to claim 22, wherein the composite fluid comprises whole blood, the first component comprises plasma, and the second component comprises platelets.

24. A method according to claim 22, wherein the composite fluid comprises whole blood, the first component comprises plasma, and the second component comprises red blood cells.

* * * * *